(12) United States Patent
Shibata et al.

(10) Patent No.: US 10,550,376 B2
(45) Date of Patent: Feb. 4, 2020

(54) XYLANASE

(71) Applicant: KAO CORPORATION, Chuo-ku, Toyko (JP)

(72) Inventors: Nozomu Shibata, Wakayama (JP); Mari Suetsugu, Osaka (JP)

(73) Assignee: Kao Corporation, Tokyo (JP)

( * ) Notice: Subject to any disclaimer, the term of this patent is extended or adjusted under 35 U.S.C. 154(b) by 121 days.

(21) Appl. No.: 15/738,211

(22) PCT Filed: Jun. 16, 2016

(86) PCT No.: PCT/JP2016/067996
§ 371 (c)(1),
(2) Date: Dec. 20, 2017

(87) PCT Pub. No.: WO2016/208492
PCT Pub. Date: Dec. 29, 2016

(65) Prior Publication Data
US 2018/0179507 A1 Jun. 28, 2018

(30) Foreign Application Priority Data
Jun. 26, 2015 (JP) ................ 2015-128823

(51) Int. Cl.
| | |
|---|---|
| *C12N 15/56* | (2006.01) |
| *C12N 9/24* | (2006.01) |
| *C12P 19/02* | (2006.01) |
| *C12P 19/14* | (2006.01) |
| *C12N 15/70* | (2006.01) |
| *C12N 15/75* | (2006.01) |
| *C12N 15/80* | (2006.01) |

(52) U.S. Cl.
CPC ........... *C12N 9/2482* (2013.01); *C12N 15/70* (2013.01); *C12N 15/75* (2013.01); *C12N 15/80* (2013.01); *C12P 19/14* (2013.01); *C12Y 302/01136* (2013.01)

(58) Field of Classification Search
None
See application file for complete search history.

(56) References Cited

U.S. PATENT DOCUMENTS

| | | |
|---|---|---|
| 6,228,630 B1 | 5/2001 | Kofod et al. |
| 8,129,591 B2 | 3/2012 | Brown et al. |
| 8,580,536 B2 | 11/2013 | McBrayer et al. |
| 2014/0287465 A1 | 9/2014 | Spodsberg et al. |

FOREIGN PATENT DOCUMENTS

| | | |
|---|---|---|
| JP | 2011-515089 A | 5/2011 |
| JP | 2012-029678 A | 2/2012 |
| WO | WO 02/24926 A1 | 3/2002 |
| WO | WO 2009/117689 A1 | 9/2009 |
| WO | WO 2013/096294 A1 | 6/2013 |

OTHER PUBLICATIONS

Definition of "preprotein" obtained from medical-dictionary.com, 1 page, last viewed on Jun. 18, 2019 (Year: 2019).*
Witkowski et al., Biochemistry 38:11643-11650, 1999 (Year: 1999).*
Shibata et al., Biotechnol. Biofuels 10:278, 2017, 17 pages (Year: 2017).*
International Search Report (ISR) for PCT/JP2016/067996; I.A. fd Jun. 16, 2016, dated Aug. 9, 2016 from the Japan Patent Office, Tokyo, Japan.
International Preliminary Report on Patentability (IPRP), Chapter I of the Patent Cooperation Treaty, including the Written Opinion PCT/JP2016/067996; I.A. fd Jun. 16, 2016, dated Dec. 26, 2017, by the International Bureau of WIPO, Geneva, Switzerland.

* cited by examiner

*Primary Examiner* — David Steadman
(74) *Attorney, Agent, or Firm* — Sterne, Kessler, Goldstein & Fox P.L.L.C.

(57) ABSTRACT

Provided is a novel xylanase having high xylanase activity. A protein consisting of an amino acid sequence described in the following (a), (b) or (c) and having xylanase activity: (a) the amino acid sequence set forth in positions 23 to 404 of SEQ ID NO: 2; (b) an amino acid sequence having at least 90% identity to the amino acid sequence set forth in positions 23 to 404 of SEQ ID NO: 2; (c) an amino acid sequence modified from the amino acid sequence set forth in positions 23 to 404 of SEQ ID NO: 2 by deletion, insertion, substitution, or addition of one or more amino acids.

20 Claims, No Drawings
Specification includes a Sequence Listing.

SEQUENCE LISTING

<160> NUMBER OF SEQ ID NOS: 19

<210> SEQ ID NO 1
<211> LENGTH: 1215
<212> TYPE: DNA
<213> ORGANISM: Penicillium sp.

<400> SEQUENCE: 1

```
atggtttgct tgtctaccaa agcactgctc ctcggagctg ccactctacc acagcttgtt      60
cactctgcgg gtcttgacac agctgctgta gctcttggaa agaaatactt cggaactgcc     120
acagataatc cagagttgac cgatacagca tacgtggccc agctgaacaa cacccaggac     180
ttcggccaga tcacacctgg aaattctcag aagtgggatg ctaccgagcc gtcacaaaac     240
acgttcacct tcacgaatgg cgacgtgatt gctgatctgg ctgaagctaa cggccaaaag     300
ctgcgatgcc acaatcttgt gtggtatgaa cagctaccta gctgggtttc cagcggaacc     360
tggaccaacg caaccctcct cgcagcgatg aagaaccata taaccaacgt cgtgactcac     420
tacaagggac agtgctacgc ctgggacgtt gtcaatgaag gtctcaacga cgacggaaca     480
taccgtgaca acatcttcta ccaatacatt ggtgaagcat acatcccaat tgcctttgcg     540
acagccgctg ccgccgaccc gagcgtcaag ctctactata cgactacaa catcgagtcc     600 gcaggagcca agtccaccgc tgcgcaaaac atcgtcaagc tggtcaagtc atacggtgtc     660
aagatcgatg gtgttggtct ccaatctcac ttcattgttg gaagcacacc cagccagagc     720
gcacaggcta gcaacatggc tgcgtttact gctctcggcg tcgaggtcgc tattactgag     780
ttggatatcc gtatgacctt gccctctacc gatgctttgc tcgcccagca aaagacagac     840
tatgcgagca ccgttgccgc ttgtgcgcaa acgagcggct gcgttggtat cacgatctgg     900
gactggacgg acaagtactc atgggtcccg aacactttct ctggacaggg tgcggcatgc     960
ccgtgggatg cgaacttggt gaagaagcca gcttataccg gcatcttgac tgcgctgggt    1020
ggtactgcca cgagcaccgc cacgacaact gcaaagacta ccttgactac tagcaccacc    1080
tcatctgggt cctctagtac gagtgttgcg cagaagtggg ggcaatgcgg tggtagtggc    1140
tggaccggac caacgacttg tgtcagtggc accacctgca cctactccaa tgcttggtac    1200
tcgcaatgtc tttga                                                     1215
```

```
<210> SEQ ID NO 2
<211> LENGTH: 404
<212> TYPE: PRT
<213> ORGANISM: Penicillium sp.

<400> SEQUENCE: 2

Met Val Cys Leu Ser Thr Lys Ala Leu Leu Gly Ala Ala Thr Leu
1               5                   10                  15

Pro Gln Leu Val His Ser Ala Gly Leu Asp Thr Ala Ala Val Ala Leu
            20                  25                  30

Gly Lys Lys Tyr Phe Gly Thr Ala Thr Asp Asn Pro Glu Leu Thr Asp
                35                  40                  45

Thr Ala Tyr Val Ala Gln Leu Asn Asn Thr Gln Asp Phe Gly Gln Ile
        50                  55                  60

Thr Pro Gly Asn Ser Gln Lys Trp Asp Ala Thr Glu Pro Ser Gln Asn
65                  70                  75                  80

Thr Phe Thr Phe Thr Asn Gly Asp Val Ile Ala Asp Leu Ala Glu Ala
                    85                  90                  95

Asn Gly Gln Lys Leu Arg Cys His Asn Leu Val Trp Tyr Glu Gln Leu
                100                 105                 110

Pro Ser Trp Val Ser Ser Gly Thr Trp Thr Asn Ala Thr Leu Leu Ala
            115                 120                 125

Ala Met Lys Asn His Ile Thr Asn Val Val Thr His Tyr Lys Gly Gln
130                 135                 140

Cys Tyr Ala Trp Asp Val Val Asn Glu Gly Leu Asn Asp Asp Gly Thr
145                 150                 155                 160

Tyr Arg Asp Asn Ile Phe Tyr Gln Tyr Ile Gly Glu Ala Tyr Ile Pro
                165                 170                 175

Ile Ala Phe Ala Thr Ala Ala Ala Asp Pro Ser Val Lys Leu Tyr
            180                 185                 190

Tyr Asn Asp Tyr Asn Ile Glu Ser Ala Gly Ala Lys Ser Thr Ala Ala
                195                 200                 205

Gln Asn Ile Val Lys Leu Val Lys Ser Tyr Gly Val Lys Ile Asp Gly
        210                 215                 220

Val Gly Leu Gln Ser His Phe Ile Val Gly Ser Thr Pro Ser Gln Ser
225                 230                 235                 240

Ala Gln Ala Ser Asn Met Ala Ala Phe Thr Ala Leu Gly Val Glu Val
                245                 250                 255

Ala Ile Thr Glu Leu Asp Ile Arg Met Thr Leu Pro Ser Thr Asp Ala
            260                 265                 270

Leu Leu Ala Gln Gln Lys Thr Asp Tyr Ala Ser Thr Val Ala Ala Cys
        275                 280                 285

Ala Gln Thr Ser Gly Cys Val Gly Ile Thr Ile Trp Asp Trp Thr Asp
        290                 295                 300

Lys Tyr Ser Trp Val Pro Asn Thr Phe Ser Gly Gln Gly Ala Ala Cys
305                 310                 315                 320

Pro Trp Asp Ala Asn Leu Val Lys Lys Pro Ala Tyr Thr Gly Ile Leu
                325                 330                 335

Thr Ala Leu Gly Gly Thr Ala Ser Thr Ala Thr Thr Ala Lys
            340                 345                 350

Thr Thr Leu Thr Thr Ser Thr Thr Ser Ser Gly Ser Ser Thr Ser
        355                 360                 365

Val Ala Gln Lys Trp Gly Gln Cys Gly Gly Ser Gly Trp Thr Gly Pro
370                 375                 380
```

Thr Thr Cys Val Ser Gly Thr Thr Cys Thr Tyr Ser Asn Ala Trp Tyr
385                 390                 395                 400

Ser Gln Cys Leu

<210> SEQ ID NO 3
<211> LENGTH: 5756
<212> TYPE: DNA
<213> ORGANISM: Trichoderma reesei

<400> SEQUENCE: 3

```
aaatctacac gtgggcccct tcggtatac tgcgtgtgtc ttctctaggt gccattcttt      60
tcccttcctc tagtgttgaa ttgtttgtgt tggagtccga gctgtaacta cctctgaatc    120
tctggagaat ggtggactaa cgactaccgt gcacctgcat catgtatata atagtgatcc    180
tgagaagggg ggtttggagc aatgtgggac tttgatggtc atcaaacaaa gaacgaagac    240
gcctcttttg caaagttttg tttcggctac ggtgaagaac tggatacttg ttgtgtcttc    300
tgtgtatttt tgtggcaaca agaggccaga gacaatctat tcaaacacca gcttgctct    360
tttgagctac aagaacctgt ggggtatata tctagagttg tgaagtcggt aatcccgctg    420
tatagtaata cgagtcgcat ctaaatactc gaagctgct gcgaacccgg agaatcgaga    480
tgtgctggaa agcttctagc gagcggctaa attagcatga aaggctatga gaaattctgg    540
agacggcttg ttgaatcatg gcgttccatt cttcgacaag caaagcgttc cgtcgcagta    600
gcaggcactc attcccgaaa aaactcggag attcctaagt agcgatggaa ccggaataat    660
ataataggca atacattgag ttgcctcgac ggttgcaatg caggggtact gagcttggac    720
ataactgttc cgtaccccac ctcttctcaa cctttggcgt ttccctgatt cagcgtaccc    780
gtacaagtcg taatcactat taacccagac tgaccggacg tgttttgccc ttcatttgga    840
gaaataatgt cattgcgatg tgtaatttgc ctgcttgacc gactggggct gttcgaagcc    900
cgaatgtagg attgttatcc gaactctgct cgtagaggca tgttgtgaat ctgtgtcggg    960
caggacacgc ctcgaaggtt cacggcaagg gaaaccaccg atagcagtgt ctagtagcaa   1020
cctgtaaagc cgcaatgcag catcactgga aaatacaaac caatggctaa agtacataa    1080
gttaatgcct aaagaagtca tataccagcg gctaataatt gtacaatcaa gtggctaaac   1140
gtaccgtaat ttgccaacgg cttgtgggt tgcagaagca acggcaaagc cccacttccc    1200
cacgtttgtt tcttcactca gtccaatctc agctggtgat ccccaattg ggtcgcttgt    1260
ttgttccggt gaagtgaaag aagacagagg taagaatgtc tgactcggag cgttttgcat   1320
acaaccaagg gcagtgatgg aagacagtga atgttgaca ttcaaggagt atttagccag    1380
ggatgcttga gtgtatcgtg taaggaggtt tgtctgccga tacgacgaat actgtatagt   1440
cacttctgat gaagtggtcc atattgaaat gtaagtcggc actgaacagg caaaagattg   1500
agttgaaact gcctaagatc tcgggccctc gggccttcgg cctttgggtg tacatgtttg   1560
tgctccgggc aaatgcaaag tgtggtagga tcgaacacac tgctgccttt accaagcagc   1620
tgagggtatg tgataggcaa atgttcaggg gccactgcat ggtttcgaat agaaagagaa   1680
gcttagccaa gaacaatagc cgataaagat agcctcatta aacggaatga gctagtaggc   1740
aaagtcagcg aatgtgtata tataaaggtt cgaggtccgt gcctccctca tgctctcccc   1800
atctactcat caactcagat cctccaggag acttgtacac catcttttga ggcacagaaa   1860
cccaatagtc aaccgcggac tgcgcatcat gtatcggaag ttggccgtca tctcggcctt   1920
cttggccaca gctcgtgctc agtcggcctg cactctccaa tcggagactc acccgcctct   1980
```

```
gacatggcag aaatgctcgt ctggtggcac gtgcactcaa cagacaggct ccgtggtcat    2040
cgacgccaac tggcgctgga ctcacgctac gaacagcagc acgaactgct acgatggcaa    2100
cacttggagc tcgaccctat gtcctgacaa cgagacctgc gcgaagaact gctgtctgga    2160
cggtgccgcc tacgcgtcca cgtacggagt taccacgagc ggtaacagcc tctccattgg    2220
ctttgtcacc cagtctgcgc agaagaacgt tggcgctcgc ctttacctta tggcgagcga    2280
cacgacctac caggaattca ccctgcttgg caacgagttc tctttcgatg ttgatgtttc    2340
gcagctgccg taagtgactt accatgaacc cctgacgcta tcttcttgtt ggctcccagc    2400
tgactggcca attcaaggtg cggcttgaac ggagctctct acttcgtgtc catggacgcg    2460
gatggtggcg tgagcaagta tcccaccaac accgctggcg ccaagtacgg cacggggtac    2520
tgtgacagcc agtgtcccg cgatctgaag ttcatcaatg ccaggccaa cgttgagggc    2580
tgggagccgt catccaacaa cgcgaacacg ggcattggag acacggaag ctgctgctct    2640
gagatggata tctgggaggc caactccatc tccgaggctc ttaccccca cccttgcacg    2700
actgtcggcc aggagatctg cgagggtgat gggtgcggcg gaacttactc cgataacaga    2760
tatggcggca cttgcgatcc cgatggctgc gactggaacc cataccgcct gggcaacacc    2820
agcttctacg gccctggctc aagctttacc ctcgatacca ccaagaaatt gaccgttgtc    2880
acccagttcg agacgtcggg tgccatcaac cgatactatg tccagaatgg cgtcactttc    2940
cagcagccca cgccgagct tggtagttac tctggcaacg agctcaacga tgattactgc    3000
acagctgagg aggcagaatt cggcggatcc tctttctcag acaagggcgg cctgactcag    3060
ttcaagaagg ctacctctgg cggcatggtt ctggtcatga gtctgtggga tgatgtgagt    3120
ttgatggaca acatgcgcg ttgacaaaga gtcaagcagc tgactgagat gttacagtac    3180
tacgccaaca tgctgtggct ggactccacc tacccgacaa cgagacctc ctccacaccc    3240
ggtgccgtgc gcggaagctg ctccaccagc tccggtgtcc ctgctcaggt cgaatctcag    3300
tctcccaacg ccaaggtcac cttctccaac atcaagttcg gacccattgg cagcaccggc    3360
aaccctagcg gcggcaaccc tcccggcgga aacccgcctg caccaccac cacccgccgc    3420
ccagccacta ccactggaag ctctcccgga cctacccagt ctcactacgg ccagtgcggc    3480
ggtattggct acagcggccc cacggtctgc gccagcggca caacttgcca ggtcctgaac    3540
ccttactact ctcagtgcct gtaaagctcc gtggcgaaag cctgacgcac cggtagattc    3600
ttggtgagcc cgtatcatga cggcggcggg agctacatgg ccccgggtga tttatttttt    3660
ttgtatctac ttctgaccct tttcaaatat acggtcaact catctttcac tggagatgcg    3720
gcctgcttgg tattgcgatg ttgtcagctt ggcaaattgt ggctttcgaa acacaaaac    3780
gattccttag tagccatgca ttttaagata acggaataga agaaagagga aattaaaaaa    3840
aaaaaaaaa caaacatccc gttcataacc cgtagaatcg ccgctcttcg tgtatcccag    3900
taccacggca aagtatttc atgatcgttc aatgttgata ttgttcccgc cagtatggct    3960
ccacccccat ctccgcgaat ctcctcttct cgaacgcggt agtggcgcgc caattggtaa    4020
tgacccatag ggagacaaac agcataatag caacagtgga aattagtggc gcataattg    4080
agaacacagt gagaccatag ctggcggcct ggaaagcact gttggagacc aacttgtccg    4140
ttgcgaggcc aacttgcatt gctgtcaaga cgatgacaac gtagccgagg accgtcacaa    4200
gggacgcaaa gttgtcgcgg atgaggtctc cgtagatggc atagccggca atccgagagt    4260
agcctctcaa caggtggcct tttcgaaacc ggtaaacctt gttcagacgt cctagccgca    4320
gctcaccgta ccagtatcga ggattgacgg cagaatagca gtggctctcc aggatttgac    4380
```

```
tggacaaaat cttccagtat tcccaggtca cagtgtctgg cagaagtccc ttctcgcgtg    4440
cgagtcgaaa gtcgctatag tgcgcaatga gagcacagta ggagaatagg aacccgcgag    4500
cacattgttc aatctccaca tgaattggat gactgctggg cagaatgtgc tgcctccaaa    4560
atcctgcgtc aacagatac tctggcaggg gcttcagatg aatgcctctg ggccccaga     4620 taagatgcag ctctggattc tcggttacga tgatatcgcg agagagcacg agttggtgat    4680 ggagggacg aggaggcata ggtcggccgc aggcccataa ccagtcttgc acagcattga    4740
tcttcctcac gaggagctcc tgatgcagaa actcctccat gttgctgatt gggttgagaa    4800
tttcatcgct cctggatcgt atggttgctg gcaagaccct gcttaaccgt gccgtgtcat    4860
ggtcatctct ggtggcttcg tcgctggcct gtctttgcaa ttcgacagca aatggtggag    4920
atctctctat cgtgacagtc atggtagcga tagctaggtg tcgttgcacg cacataggcc    4980
gaaatgcgaa gtggaaagaa tttcccggcg cggaatgaag tctcgtcatt ttgtactcgt    5040
actcgacacc tccaccgaag tgttaagaat ggatccacga tgccaaaaag cttgttcatt    5100
tcggctagcc cgtgatcctg gcgcttctag ggctgaaact gtgttgttaa tgtattattg    5160
gctgtgtaac tgacttgaat ggggaatgag gagcgcgatg gattcgcttg catgtcccct    5220
ggccaagacg agccgctttg gcggtttgtg attcgaaggt gtgtcagcgg aggcgccagg    5280
gcaacacgca ctgagccagc caacatgcat tgctgccgac atgaatagac acgcgccgag    5340
cagacatagg agacgtgttg actgtaaaaa ttctactgaa tattagcacg catggtctca    5400
ataagagcaa taggaatgct tgccaatcat aagtacgtat gtgcttttc ctgcaaatgg     5460 tacgtacgga cagttcatgt tgtctgtcat cccccactca ggctctcatg atcattttat    5520
gggactgggg ttttgctgac tgaatggatt cagccgcacg aaacaaattg ggggccatgc    5580
agaagggaag cccccccagc cccctgttca taatttgtta agagtcggag agctgcctag    5640
tatgaagcag caattgataa cgttgacttt gcgcatgagc tctgaagccg gcatatgta     5700 tcacgtttct gcctagagcc gcacgggacc caagaagctc ttgtcataag gtattt        5756
```

<210> SEQ ID NO 4
<211> LENGTH: 3089
<212> TYPE: DNA
<213> ORGANISM: Aspergillus nidurans

<400> SEQUENCE: 4

```
tgcgcacatc attggatagg cagattactc agcctgaatg acatcaacat gttacccatg      60
atacaatagg tcacacaaac aagcgctaag atgcacttgg tatgacaagc ccagtagtcc     120
gtttcaaaag acctagatga tgaactacaa catgaggtgt tgcctcctga tccagtccaa     180
ctgcaaacgc tgatgtatac tcaatcaagc ctgatgtaaa tgctgcgact cgattcgctg     240
gatatgaaga tcaaagagag ctctgatggg tccaatatag ccgggttttg ttaggacagt     300
ccaccacacc gatattagaa ttggtcaagc accttatcat ttcatagaga ttgcggtttc     360
tagatctacg ccaggaccga gcaagcccag atgagaaccg acgcagattt ccttggcacc     420
tgttgcttca gctgaatcct ggcaatacga gataccttgct ttgaatattt tgaatagctc    480
gcccgctgga gagcatcctg aatgcaagta acaaccgtag aggctgacac ggcaggtgtt     540
gctagggagc gtcgtgttct acaaggccag acgtcttcgc ggttgatata tatgtatgtt    600
tgactgcagg ctgctcagcg acgacagtca agttcgccct cgctgcttgt gcaataatcg     660
cagtggggaa gccacaccgt gactcccatc tttcagtaaa gctctgttgg tgtttatcag     720
caatacacgt aatttaaact cgttagcatg gggctgatag cttaattacc gtttaccagt     780
```

```
gccgcggttc tgcagctttc cttggcccgt aaaattcggc gaagccagcc aatcaccagc    840
taggcaccag ctaaaccctd taattagtct cttatcaaca ccatccgctc ccccgggatc    900
aatgaggaga atgaggggga tgcggggcta agaagccta cataaccctc atgccaactc    960
ccagtttaca ctcgtcgagc caacatcctg actataagct aacacagaat gcctcaatcc    1020
tgggaagaac tggccgctga taagcgcgcc cgcctcgcaa aaaccatccc tgatgaatgg    1080
aaagtccaga cgctgcctgc ggaagacagc gttattgatt cccaaagaa atcggggatc    1140 cttttcagagg ccgaactgaa gatcacagag gcctccgctg cagatcttgt gtccaagctg    1200
gcggccggag agttgacctc ggtggaagtt acgctagcat tctgtaaacg ggcagcaatc    1260
gcccagcagt tagtagggtc ccctctacct ctcagggaga tgtaacaacg ccaccttatg    1320
ggactatcaa gctgacgctg gcttctgtgc agacaaactg cgcccacgag ttcttccctg    1380
acgccgctct cgcgcaggca agggaactcg atgaatacta cgcaaagcac aagagacccg    1440
ttggtccact ccatggcctc cccatctctc tcaaagacca gcttcgagtc aaggtacacc    1500
gttgccccta agtcgttaga tgtccctttt tgtcagctaa catatgccac cagggctacg    1560
aaacatcaat gggctacatc tcatggctaa acaagtacga cgaaggggac tcggttctga    1620
caaccatgct ccgcaaagcc ggtgccgtct tctacgtcaa gacctctgtc ccgcagaccc    1680
tgatggtctg cgagacagtc aacaacatca tcgggcgcac cgtcaaccca cgcaacaaga    1740
actggtcgtg cggcggcagt tctggtggtg agggtgcgat cgttgggatt cgtggtggcg    1800
tcatcggtgt aggaacggat atcggtggct cgattcgagt gccggccgcg ttcaacttcc    1860
tgtacggtct aaggccgagt catgggcggc tgccgtatgc aaagatggcg aacagcatgg    1920
agggtcagga gacggtgcac agcgttgtcg ggccgattac gcactctgtt gagggtgagt    1980
ccttcgcctc ttccttcttt tcctgctcta taccaggcct ccactgtcct cctttcttgc    2040
tttttatact atatacgaga ccggcagtca ctgatgaagt atgttagacc tccgcctctt    2100
caccaaatcc gtcctcggtc aggagccatg gaaatacgac tccaaggtca tccccatgcc    2160
ctggcgccag tccgagtcgg acattattgc ctccaagatc aagaacggcg ggctcaatat    2220
cggctactac aacttcgacg gcaatgtcct tccacaccct cctatcctgc gcggcgtgga    2280
aaccaccgtc gccgcactcg ccaaagccgg tcacaccgtg accccgtgga cgccatacaa    2340
gcacgatttc ggccacgatc tcatctccca tatctacgcg gctgacggca gcgccgacgt    2400
aatgcgcgat atcagtgcat ccggcgagcc ggcgattcca aatatcaaag acctactgaa    2460
cccgaacatc aaagctgtta acatgaacga gctctgggac acgcatctcc agaagtggaa    2520
ttaccagatg gagtaccttg agaaatggcg ggaggctgaa gaaaaggccg ggaaggaact    2580
ggacgccatc atcgcgccga ttacgcctac cgctgcggta cggcatgacc agttccggta    2640
ctatgggtat gcctctgtga tcaacctgct ggatttcacg agcgtggttg ttccggttac    2700
ctttgcggat aagaacatcg ataagaagaa tgagagtttc aaggcggtta gtgagcttga    2760
tgccctcgtg caggaagagt atgatccgga ggcgtaccat ggggcaccgg ttgcagtgca    2820
ggttatcgga cggagactca gtgaagagag gacgttggcg attgcagagg aagtggggaa    2880
gttgctggga aatgtggtga ctccatagct aataagtgtc agatagcaat ttgcacaaga    2940
aatcaatacc agcaactgta ataagcgct gaagtgacca tgccatgcta cgaaagagca    3000
gaaaaaaacc tgccgtagaa ccgaagagat atgacacgct tccatctctc aaaggaagaa    3060
tcccttcagg gttgcgtttc cagtgcgca                                        3089
```

```
<210> SEQ ID NO 5
<211> LENGTH: 35
<212> TYPE: DNA
<213> ORGANISM: Artificial sequence
<220> FEATURE:
<223> OTHER INFORMATION: Oligonucleotide primer

<400> SEQUENCE: 5
cgtttccagt gcgcagaccg tcacaaggga cgcaa                              35

<210> SEQ ID NO 6
<211> LENGTH: 35
<212> TYPE: DNA
<213> ORGANISM: Artificial sequence
<220> FEATURE:
<223> OTHER INFORMATION: Oligonucleotide primer

<400> SEQUENCE: 6
ccaatgatgt gcgcactcgg ctacgttgtc atcgt                              35

<210> SEQ ID NO 7
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 7
tgcgcacatc attggatagg                                               20

<210> SEQ ID NO 8
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 8
tgcgcactgg aaacgcaacc                                               20

<210> SEQ ID NO 9
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 9
taaagctccg tggcgaaagc                                               20

<210> SEQ ID NO 10
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 10
gatgcgcagt ccgcggttga                                               20

<210> SEQ ID NO 11
<211> LENGTH: 35
<212> TYPE: DNA
<213> ORGANISM: Artificial sequence
<220> FEATURE:
<223> OTHER INFORMATION: Oligonucleotide primer
```

<400> SEQUENCE: 11
cgcggactgc gcatcatggt ttgcttgtct accaa                       35

<210> SEQ ID NO 12
<211> LENGTH: 35
<212> TYPE: DNA
<213> ORGANISM: Artificial sequence
<220> FEATURE:
<223> OTHER INFORMATION: Oligonucleotide primer

<400> SEQUENCE: 12
cgccacggag ctttaaagac attgcgagta ccaag                       35

<210> SEQ ID NO 13
<211> LENGTH: 752
<212> TYPE: DNA
<213> ORGANISM: Trichoderma reesei

<400> SEQUENCE: 13
atggttgcct tttccagcct catctgcgct ctcaccagca tcgccagtac tctggcgatg      60
cccacaggcc tcgagcctga gagcagtgtc aacgtcacag agcgtggcat gtacgacttt     120
gttcttggag ctcacaatga tcatcgccgt cgtgctagca tcaactacga ccaaaactac     180
caaactggcg gacaagtcag ctattcgcct tccaacactg gcttctcagt gaactggaac     240
actcaagatg acttttgttgt gggcgttggt tggacgactg atcttctgc gtaggaggac     300 tcctcatcat tctgcacttt gaaagcatct tctgaccaaa agcttctctt agtcccatca     360
actttggcgg ctcttttagt gtcaacagcg gaactggcct gctttccgtc tatggctgga     420
gcaccaaccc actggttgag tactacatca tggaggacaa ccacaactac ccagcacagg     480
gtaccgtcaa gggaaccgtc accagcgacg gagccactta ccatcctgg gagaataccc      540 gtgtcaacga gccttccatc agggcacag cgaccttcaa ccagtacatt tccgtgcgga      600
actcgcccag gaccagcgga actgttactg tgcagaacca cttcaatgct gggcctcgc      660 ttggcctgca ccttgggcag atgaactacc aggttgtcgc tgtcgaaggc tggggtggta     720
gtggttctgc ctcacagagt gtcagcaact ag                                  752

<210> SEQ ID NO 14
<211> LENGTH: 781
<212> TYPE: DNA
<213> ORGANISM: Trichoderma reesei

<400> SEQUENCE: 14
atggtctcct tcacctccct cctcgccggc gtcgccgcca tctcgggcgt cttggccgct      60
cccgccgccg aggtcgaatc cgtggctgtg gagaagcgcc agacgattca gcccggcacg     120
ggctacaaca acggctactt ctactcgtac tggaacgatg gccacggcgg cgtgacgtac     180
accaatggtc ccggcgggca gttctccgtc aactggtcca actcgggcaa ctttgtcggc     240
ggcaagggat ggcagcccgg caccaagaac aagtaagact acctactctt accccctttg     300
accaacacag cacaacacaa tacaacacat gtgactacca atcatggaat cggatctaac     360
agctgtgttt tcaaaaaaaa gggtcatcaa cttctcgggc agctacaacc caacggcaa     420 cagctacctc tccgtgtacg gctggtcccg caaccccctg atcgagtact acatcgtcga     480
gaactttggc acctacaacc cgtccacggg cgccaccaag ctgggcgagg tcacctccga     540
cggcagcgtc tacgacattt accgcacgca gcgcgtcaac cagccgtcca tcatcggcac     600
cgccaccttt taccagtact ggtccgtccg ccgcaaccac cgctcgagcg gctccgtcaa     660

```
cacggcgaac cacttcaacg cgtgggctca gcaaggcctg acgctcggga cgatggatta    720
ccagattgtt gccgtggagg gttactttag ctctggctct gcttccatca ccgtcagcta    780
a                                                                    781

<210> SEQ ID NO 15
<211> LENGTH: 38
<212> TYPE: DNA
<213> ORGANISM: Artificial sequence
<220> FEATURE:
<223> OTHER INFORMATION: Oligonucleotide primer

<400> SEQUENCE: 15
caccaccacc accaccacta aagctccgtg gcgaaagc                             38

<210> SEQ ID NO 16
<211> LENGTH: 35
<212> TYPE: DNA
<213> ORGANISM: Artificial sequence
<220> FEATURE:
<223> OTHER INFORMATION: Oligonucleotide primer

<400> SEQUENCE: 16
cgcggactgc gcatcatggt tgccttttcc agcct                                35

<210> SEQ ID NO 17
<211> LENGTH: 35
<212> TYPE: DNA
<213> ORGANISM: Artificial sequence
<220> FEATURE:
<223> OTHER INFORMATION: Oligonucleotide primer

<400> SEQUENCE: 17
gtggtggtgg tggtggttgc tgacactctg tgagg                                35

<210> SEQ ID NO 18
<211> LENGTH: 35
<212> TYPE: DNA
<213> ORGANISM: Artificial sequence
<220> FEATURE:
<223> OTHER INFORMATION: Oligonucleotide primer

<400> SEQUENCE: 18
cgcggactgc gcatcatggt ctccttcacc tccct                                35

<210> SEQ ID NO 19
<211> LENGTH: 35
<212> TYPE: DNA
<213> ORGANISM: Artificial sequence
<220> FEATURE:
<223> OTHER INFORMATION: Oligonucleotide primer

<400> SEQUENCE: 19
gtggtggtgg tggtggctga cggtgatgga agcag                                35
```

XYLANASE

FIELD OF THE INVENTION

The present invention relates to a novel xylanase.

BACKGROUND OF THE INVENTION

A technique has been previously known to manufacture sugar from the cellulose in a cellulose-containing biomass material (which hereinafter may be referred to as "biomass") and convert it into ethanol, lactic acid, and the like by fermentation method etc. More recently, development of a technique to efficiently utilize biomass as resources is drawing attention in terms of approach to environmental problems.

Biomass is consisted of cellulose fibers as well as hemicellulose mainly containing xylan and lignin surrounding the fibers. Development of an enzyme which efficiently hydrolyzes cellulose and hemicellulose is required to increase the efficiency of saccharification of cellulose and hemicellulose in biomass.

Saccharification of biomass by a cellulase and enzymatic degradation of biomass by a hemicellulase and a ligninase have been conventionally conducted. For example, an enzyme composition has been developed in which a hemicellulase such as a xylanase or an arabinofuranosidase derived from *Trichoderma reesei* is added to a cellulase (Patent Literature 1). A protein having xylanase activity derived from microorganism groups present in bagasse compost and a method of manufacturing sugar by reacting the protein and a cellulase with biomass resources have been known (Patent Literature 2).

A xylanase and an enzyme composition comprising it have been developed. Patent Literature 3 describes an enzyme composition used for the degradation of cellulosic material comprising a family 10 xylanase derived from *Trichophaea saccata* or *Aspergillus fumigatus* and a family 11 xylanase derived from *Thermobifida fusca* etc. Patent Literature 4 describes a xylanase derived from *Penicillium* sp. Patent Literature 5 describes a xylanase and a variant thereof obtained from *Talaromyces emersonii*. Patent Literature 6 describes a xylanase derived from *Aspergillus aculeatus*. A xylanase preparation manufactured and sold by Novozymes (such as Cellic® HTec) is also known.
[Patent Literature 1] JP-A-2011-515089
[Patent Literature 2] JP-A-2012-029678
[Patent Literature 3] U.S. Pat. No. 8,580,536
[Patent Literature 4] U.S. Pat. No. 8,129,591
[Patent Literature 5] WO2002/024926
[Patent Literature 6] U.S. Pat. No. 6,228,630

SUMMARY OF THE INVENTION

In one aspect, the present invention provides a protein consisting of an amino acid sequence described in the following (a), (b) or (c) and having xylanase activity.

(a) an amino acid sequence set forth in positions 23 to 404 of SEQ ID NO: 2;

(b) an amino acid sequence having at least 90% identity to the amino acid sequence set forth in positions 23 to 404 of SEQ ID NO: 2;

(c) an amino acid sequence modified from the amino acid sequence set forth in positions 23 to 404 of SEQ ID NO: 2 by deletion, insertion, substitution, or addition of one or more amino acids.

In a further aspect, the present invention provides a polynucleotide encoding a protein having the above described xylanase activity.

In a further aspect, the present invention provides a vector comprising the above described polynucleotide.

In a further aspect, the present invention provides a method of manufacturing a transformant, comprising introducing the above described polynucleotide or vector into a host.

In a further aspect, the present invention provides a transformant in which the above described polynucleotide or vector is introduced.

In a further aspect, the present invention provides a biomass saccharifying agent comprising a protein having the above described xylanase activity.

In a further aspect, the present invention provides a method of manufacturing sugar from biomass, comprising using a protein having the above described xylanase activity or the above described biomass saccharifying agent.

DETAILED DESCRIPTION OF THE INVENTION (1. Definition)

Herein, the identity of a nucleotide sequence and an amino acid sequence is calculated by Lipman-Pearson Method (Science, 1985, 227: 1435-1441). Specifically, the identity is calculated by analyzing sequences with setting Unit size to compare (ktup) at 2 using the homology search (Search homology) program of the genetic information processing software Genetyx-Win.

As used herein, "at least 90% identity" with reference to an amino acid sequence or a nucleotide sequence refers to 90% or more, preferably 95% or more, more preferably 97% or more, further preferably 98% or more, and still preferably 99% or more identity.

As used herein, examples of "an amino acid sequence modified by deletion, insertion, substitution, or addition of one or more amino acids" include an amino acid sequence modified by deletion, insertion, substitution, or addition of 1 or more to 30 or less, preferably 20 or less, more preferably 10 or less, and further preferably 5 or less amino acids. As used herein, examples of "a nucleotide sequence modified by deletion, insertion, substitution, or addition of one or more nucleotides" include a nucleotide sequence modified by deletion, insertion, substitution, or addition of 1 or more to 90 or less, preferably 60 or less, more preferably 30 or less, further preferably 15 or less, and further more preferably 10 or less nucleotides.

As used herein, "a corresponding position" or "a corresponding region" relative to the specific position or region on the specific amino acid sequence or nucleotide sequence on an amino acid sequence or a nucleotide sequence of interest can be determined by aligning (alignment) the amino acid sequence or the nucleotide sequence of interest with the specific sequence as a standard (reference sequence) so that conserved amino acid residues or nucleotides present in amino acid sequences or nucleotide sequences have maximum homology. The alignment can be performed using a known algorithm, the procedure of which is known to those skilled in the art. Though the alignment can be performed manually for example based on the Lipman-Pearson Method above etc., it can be performed using the Clustal W multiple alignment program (Thompson, J. D. et al, 1994, Nucleic Acids Res., 22: 4673-4680) in a default setting. Alternatively, Clustal W2 and Clustal omega, the revision of Clustal W, can also be used. Clustal W, Clustal W2 and Clustal omega are for example available on websites of European Bioinformatics Institute (EBI [available on the world wide web at ebi.ac.uk/index.html]) and DNA Data Bank of Japan (DDBJ [available on the world wide web at ddbj.nig.ac.jp/Welcome-j.html]) managed by National Institute for Genetics.

As used herein, "xylanase activity" refers to the activity which hydrolyzes a xylose β-1,4-glycosidic bond of xylan. The xylanase activity of a protein can be determined by reacting the protein with xylan as a substrate and measuring the amount of a degradation product of xylan. Preferably, 1 unit (U) of xylanase activity of a protein herein is defined as the amount of the protein required to release 1 micromole of a reducing sugar per minute from xylan when the protein produces a reducing sugar from xylan as a substrate for 15 min at pH 5.0, 60° C. The xylanase activity of a protein can be measured by quantifying the reducing sugar produced from xylan with 3,5-dinitrosalicylic acid (DNS) method. In a more specified example, soluble xylan, sodium acetate buffer (pH 5.0) and a protein of interest are mixed and reacted at 60° C., and then, the DNS solution (a solution comprising sodium hydroxide, 3,5-dinitrosalicylic acid and potassium sodium tartrate) is added to the mixture and the mixture is reacted at around 100° C., and then the absorbance of the reaction solution is measured at the wavelength of 540 nm. The amount of a reducing sugar is quantified by standardizing measured value with reference to the standard curve made using xylose. The xylanase activity can be calculated based on the measured amount of a reducing sugar. The specific procedure of xylanase activity measurement by DNS method is described in Examples below.

As used herein, "a xylanase" refers to a protein having the activity which hydrolyzes a xylose glycosidic bond of xylan (i.e. having xylanase activity).

As used herein, "biomass" refers to cellulosic and/or lignocellulosic biomass comprising a hemicellulose component produced by a plant and an alga. Specific examples of biomass include one or more selected from the group consisting of a variety of woods obtained from a conifer such as a larch and Taxodium as well as a broad-leaved tree such as an oil palm (trunk part) and a hinoki; a processed product or a ground product of a wood such as wood chips; pulp such as wood pulp manufactured from a wood and cotton linter pulp obtained from fiber around a cotton seed; paper such as newspaper, corrugated board, a magazine and fine quality paper; a stalk, a leaf, a bunch etc. of a plant such as bagasse (pomace of sugar cane), palm Empty Fruit Bunch (EFB), oil palm (trunk part), Erianthus, rice straw, and corn stalk or leaf; a hull of a plant such as chaff, a palm hull and a coconut hull; an alga etc. Among these, wood, a processed product or ground product of wood and a stalk, a leaf and a bunch of a plant etc. are preferred, and bagasse, EFB, oil palm (trunk part) and Erianthus are more preferred, and bagasse is further preferred in terms of ready availability and cost of raw materials. The biomass can be used alone, or 2 or more types of biomass can be mixed to use. The biomass can be dried.

(2. Xylanase)

A conventional method of saccharifying biomass using a hemicellulase and a xylanase has not yet been satisfying in terms of saccharification efficiency or cost of enzyme. The present invention relates to a novel xylanase capable of saccharifying biomass more efficiently and economically.

The present inventors found a novel xylanase having high xylanase activity and capable of achieving extremely highly efficient saccharification of biomass when the xylanase is combined with other enzymes related to saccharification of biomass.

The present invention provides a novel xylanase. The xylanase of the present invention or an enzyme composition comprising it can achieve more efficient saccharification of biomass compared with the case using a conventionally known xylanase or an enzyme composition comprising it. Therefore, one can manufacture sugar from biomass efficiently and inexpensively according to the present invention.

The xylanase of the present invention can be a protein consisting of an amino acid sequence described in the following (a), (b) or (c) and having xylanase activity.

(a) an amino acid sequence set forth in positions 23 to 404 of SEQ ID NO: 2;

(b) an amino acid sequence having at least 90% identity to the amino acid sequence set forth in positions 23 to 404 of SEQ ID NO: 2;

(c) an amino acid sequence modified from the amino acid sequence set forth in positions 23 to 404 of SEQ ID NO: 2 by deletion, insertion, substitution, or addition of one or more amino acids.

In one embodiment, the xylanase of the present invention is a protein consisting of an amino acid sequence set forth in positions 23 to 404 of SEQ ID NO: 2. Preferred examples of the xylanase include a xylanase derived from *Penicillium* sp. consisting of an amino acid sequence set forth in positions 23 to 404 of SEQ ID NO: 2.

In another embodiment, the xylanase of the present invention is a protein consisting of an amino acid sequence having at least 906 identity to the amino acid sequence set forth in positions 23 to 404 of SEQ ID NO: 2 and having xylanase activity. In yet another embodiment, the xylanase of the present invention is a protein consisting of an amino acid sequence modified from the amino acid sequence set forth in positions 23 to 404 of SEQ ID NO: 2 by deletion, insertion, substitution, or addition of one or more amino acids and having xylanase activity. The protein can be produced, for example, by introducing a mutation into a gene encoding the xylanase consisting of an amino acid sequence set forth in positions 23 to 404 of SEQ ID NO: 2 (for example, a gene consisting of the nucleotide sequence set forth in positions 67 to 1,212 of SEQ ID NO: 1) using known mutagenesis methods such as ultraviolet irradiation and site-directed mutagenesis, expressing the obtained mutated genes, and selecting a protein having xylanase activity from expressed gene products. Procedures for producing such a mutant are known to those skilled in the art.

The xylanase of the present invention has an amino acid sequence differing from a xylanase which has been conventionally isolated or purified. For example, a known xylanase having an amino acid sequence with highest sequence identity to the xylanase of the present invention set forth in the positions 23 to 404 of SEQ ID NO: 2 is the xylanase derived from *Talaromyces emersonii* described in Patent Literature 5 and the sequence identity is 77%.

Preferably, the xylanase of the present invention further has the following enzymatic properties.

(i) pH Dependence

The xylanase activity of the xylanase of the present invention is preferably 70% or more, more preferably 80% or more, further preferably 85% or more, and still preferably 90% or more of the maximal activity in the range of pH 45 to 5.5 at a reaction temperature of 60° C. Here, "maximal activity" refers to the xylanase activity at an optimum reaction pH at a reaction temperature of 60° C.

(ii) Optimum Reaction pH

As used herein, "optimum reaction pH for xylanase activity" refers to pH in which the activity of degradation of xylan is maximal at 60° C., and specifically, the pH can be measured according to the method described in Examples below. The optimum reaction pH of the xylanase activity of the xylanase of the present invention is preferably in the range of pH of from 3.8 to 6.0, and more preferably pH of from 4.0 to 5.5.

(iii) Optimum Reaction Temperature

As used herein, "optimum reaction temperature for xylanase activity" refers to a temperature at which xylanase activity is maximal at the optimum pH, and specifically, the temperature is measured according to the method described in Examples below. In the xylanase of the present invention, the optimum reaction temperature of xylanase activity is preferably from 65 to 80° C., and more preferably from 70 to 78° C.

(iv) Maximal Activity

As used herein, "maximal activity" of a xylanase refers to specific activity of xylanase activity at an optimum pH at 60° C. "Maximal activity" of the xylanase of the present invention is preferably 400 U/mg protein or more, more preferably 450 U/mg protein or more, and further preferably 500 U/mg protein or more.

In a microbial cell, the xylanase of the present invention can be expressed as a preprotein comprising a signal sequence and then the signal sequence can be cleaved to produce the xylanase of the present invention as a mature protein.

Therefore, the present invention also provides a xylanase preprotein consisting of an amino acid sequence further comprising an amino acid sequence set forth in positions 1 to 22 of SEQ ID NO: 2 N-terminal to an amino acid sequence described in the (a), (b) or (c).

Alternatively, the present invention provides a xylanase preprotein consisting of an amino acid sequence described in the following (a'), (b') or (c').

(a') an amino acid sequence set forth in SEQ ID NO: 2;

(b') an amino acid sequence having at least 900 identity to the amino acid sequence set forth in SEQ ID NO: 2;

(c') an amino acid sequence modified from the amino acid sequence set forth in SEQ ID NO: 2 by deletion, insertion, substitution, or addition of one or more amino acids.

Preferably, the region corresponding to positions 1 to 22 of SEQ ID NO: 2 in the amino acid sequence described in the (a'), (b') or (c') has a function as a secretory signal sequence.

(3. Polynucleotide, Vector and Transformant)

The xylanase of the present invention can be produced, for example, by expressing a gene encoding the xylanase of the present invention. Preferably, the xylanase of the present invention can be produced from a transformant in which the polynucleotide encoding the xylanase of the present invention is introduced. For example, the xylanase of the present invention is produced from the polynucleotide encoding the xylanase of the present invention introduced in a transformant after the polynucleotide encoding the xylanase of the present invention or a vector comprising it is introduced into a host to obtain a transformant and the transformant is cultured in an appropriate medium. The xylanase of the present invention can be obtained by isolating or purifying the produced xylanase from the culture.

Therefore, the present invention further provides a polynucleotide encoding the xylanase of the present invention and a vector comprising it. The present invention further provides a method of manufacturing a transformant, comprising introducing a polynucleotide encoding the xylanase of the present invention or a vector comprising it into a host. The present invention further provides a transformant comprising a polynucleotide encoding the xylanase of the present invention or a vector comprising it introduced from the outside of a cell. The present invention further provides a method of manufacturing the xylanase of the present invention, comprising culturing the transformant.

The polynucleotide encoding the xylanase of the present invention can be a polynucleotide consisting of an amino acid sequence described in the (a), (b) or (c) and encoding the protein having xylanase activity. The polynucleotide encoding the xylanase of the present invention can be in the form of a single-stranded or double-stranded DNA, RNA or an artificial nucleic acid, or can be a cDNA or a chemically synthesized DNA which does not comprise any intron.

Preferred examples of the polynucleotide encoding the xylanase of the present invention include a polynucleotide consisting of a nucleotide sequence described in the following (i), (ii) or (iii).

(i) a nucleotide sequence set forth in positions 67 to 1,212 of SEQ ID NO: 1;

(ii) a nucleotide sequence having at least 90% identity to the nucleotide sequence set forth in positions 67 to 1,212 of SEQ ID NO: 1;

(iii) a nucleotide sequence modified from the nucleotide sequence set forth in positions 67 to 1,212 of SEQ ID NO: 1 by deletion, insertion, substitution, or addition of one or more nucleotides.

Another preferred example of the polynucleotide encoding the xylanase of the present invention include a polynucleotide consisting of a nucleotide sequence described in the following (i'), (ii') or (iii').

(i') a nucleotide sequence set forth in SEQ ID NO: 1;

(ii') a nucleotide sequence having at least 90% identity to the nucleotide sequence set forth in SEQ ID NO: 1;

(iii') a nucleotide sequence modified from the nucleotide sequence set forth in SEQ ID NO: 1 by deletion, insertion, substitution, or addition of one or more nucleotides.

Preferably, the region corresponding to positions 1 to 66 of SEQ ID NO: 1 in the nucleotide sequence described in the (i'), (ii') or (iii') encodes a secretory signal sequence.

The polynucleotide encoding the xylanase of the present invention can be synthesized chemically or by genetic engineering based on the amino acid sequence of a xylanase. For example, the polynucleotide can be synthesized chemically based on the amino acid sequence of the xylanase of the present invention or preprotein thereof. A contract synthesis service of nucleic acid (provided from, for example, Medical & Biological Laboratories Co., Ltd., Genscript etc.) can be used for the chemical synthesis of the polynucleotide. Further, the synthesized polynucleotide can be amplified by PCR and cloning etc.

Alternatively, the polynucleotide encoding the xylanase of the present invention can be produced by introducing a mutation into the polynucleotide synthesized according to the procedure with known mutagenesis methods such as the ultraviolet irradiation and site-directed mutagenesis. For example, the polynucleotide encoding the xylanase of the present invention can be obtained by introducing a mutation into the polynucleotide of SEQ ID NO: 1 with a known method, expressing the obtained polynucleotide, investigating its xylanase activity, and selecting a polynucleotide encoding the protein having desired xylanase activity.

Site-directed mutagenesis of a polynucleotide can be performed with any methods such as, for example, inverse PCR and annealing (Muramatsu et al. edit., "Revised 4th edition New genetic engineering handbook", YODOSHA, p. 82-88). A variety of commercially available kits for site-directed mutagenesis such as QuickChange II Site-Directed Mutagenesis Kit from Stratagene and QuickChange Multi Site-Directed Mutagenesis Kit can be used as needed.

Examples of the type of a vector comprising the polynucleotide encoding the xylanase of the present invention include, without limitation, a vector usually used for gene cloning, for example, a plasmid, a cosmid, a phage, a virus, a YAC and a BAC. Among these, a plasmid vector is preferred and for example a commercially available plasmid vector for protein expression, for example, pUC19, pUC118, pUC119, pBR322 etc. (all of which are from TAKARA BIO INC.) can be preferably used.

The vector can comprise a DNA region comprising a replication initiation region or a replication origin of DNA. Alternatively, a regulatory sequence such as a promoter region for initiating transcription of the gene, a terminator region or a secretory signal region for secreting an expressed protein to the outside of a cell can be operably liked to the upstream of the polynucleotide encoding the xylanase of the present invention (i.e. the xylanase gene of the present invention) in the vector. As used herein, a gene and a regulatory sequence being "operably liked" refers to a condition in which the gene and the regulatory region are positioned so that the gene can be expressed under the regulation by the regulatory region.

The type of the regulatory sequence of a promoter region, a terminator, and a secretory signal region etc. is not specifically limited, and a promoter and a secretory signal sequence usually used can be selected to use as appropriate depending on the host into which the sequence is introduced. For example, preferred examples of the regulatory sequence which can be incorporated to the vector of the present invention include the cbh1 promoter sequence derived from *Trichoderma reesei* (Curr, Genet, 1995, 28 (1): 71-79). Alternatively, other promoters expressing a carbohydrase such as a cellobiohydrolase, an endoglucanase, a β glucosidase, a xylanase and a β xylosidase can be used. Alternatively, a promoter of an enzyme of a metabolic pathway such as a pyruvate decarboxylase, an alcohol dehydrogenase and a pyruvate kinase can be used.

Alternatively, a marker gene to select a host into which the vector is appropriately introduced (for example, a resistance gene to an agent such as ampicillin, neomycin, kanamycin and chloramphenicol) can be further incorporated into the vector of the present invention. Alternatively, a gene encoding a synthase of a required nutrient can be incorporated into the vector as a marker gene, when an auxotrophic strain is used as a host. Alternatively, a related gene of the metabolism can be incorporated into the vector as a marker gene, when a selective medium requiring specific metabolism for growth is used. Examples of such a metabolism related gene include an acetamidase gene for using acetamide as a nitrogen source.

Ligation between the polynucleotide encoding the xylanase of the present invention and a regulatory sequence and a marker gene can be performed by a known method in the art such as SOE (splicing by overlap extension) -PCR (Gene, 1989, 77: 61-68). The procedure for introducing a ligated fragment into a vector is known in the art.

Examples of a host of a transformant into which the vector is introduced include a microorganism such as a bacterium and filamentous fungus. Examples of the bacterium include *Escherichia coli* and a bacterium belonging to *Staphylococcus, Enterococcus, Listeria* and *Bacillus*, of which *Escherichia coli* and *Bacillus* bacteria (for example, *Bacillus subtilis* or a mutant thereof) are preferred. Examples of the *Bacillus subtilis* mutant can include protease 9 double deficient strain KA8AX described in J. Biosci. Bioeng., 2007, 104 (2): 135-143 and a DBPA strain, a mutant from protease 8 double deficient strain described in Biotechnol. Lett., 2011, 33 (9): 1847-1852, of which protein folding efficiency is improved. Examples of the filamentous fungus include *Trichoderma, Aspergillus* and *Rhizopus*, of which *Trichoderma* is preferred in terms of enzyme productivity.

A method usually used in the field such as protoplast method and electroporation can be used as a method of introducing a vector into a host. A transformant of interest can be obtained by selecting a strain in which a vector is appropriately introduced using an index such as the expression of a marker gene and/or auxotrophy.

Alternatively, a fragment in which the polynucleotide encoding the xylanase of the present invention, a regulatory sequence and a marker gene are ligated can be directly introduced into the genome of a host. For example, the polynucleotide encoding the xylanase of the present invention is introduced into the genome of a host by constructing a DNA fragment added with a sequence complementary to the genome of the host at both ends of the ligated fragment, introducing the fragment into the host and inducing homologous recombination between the host genome and the DNA fragment by SOE-PCR.

Culturing the thus obtained transformant, in which the polynucleotide encoding the xylanase of the present invention or a vector comprising it is introduced, in an appropriate medium results in the expression of the xylanase gene on the vector, and then the production of the xylanase of the present invention. The medium used for the culture of such transformant can be selected depending on the type of the microorganism of such transformant by those skilled in the art as appropriate.

Alternatively, the xylanase of the present invention can be expressed from the polynucleotide encoding the xylanase of the present invention or a transcription product thereof using a cell-free translation system. "Cell-free translation system" refers to an in vitro transcription-translation system or an in vitro translation system constructed by adding reagents such as amino acids required for the translation of a protein into a suspension obtained by mechanically destructing cells to be a host.

The xylanase of the present invention produced in the culture or cell-free translation system can be isolated or purified by using a general method used for the purification of a protein, for example, centrifugation, ammonium sulfate precipitation, gel chromatography, ion-exchange chromatography and affinity chromatography etc. alone or in combination as appropriate. Here, when the gene encoding the xylanase of the present invention and the secretory signal sequence are operably liked on the vector within the transformant, the produced xylanase can be collected more easily from the culture because the xylanase is secreted to the outside of a cell. The xylanase collected from the culture can be further purified with known means.

(4. Method of Saccharifying Biomass or Method of Manufacturing Sugar)

The xylanase of the present invention has remarkably higher activity to saccharify biomass compared to a conventionally known xylanase and xylanase preparation as shown in Examples below. Therefore, the xylanase of the present invention can be suitably used for the saccharification of biomass or for the manufacture of sugar from biomass. Therefore, the present invention further provides a biomass saccharifying agent comprising the xylanase of the present invention. The present invention further provides a method of saccharifying biomass, comprising using the xylanase of the present invention or the biomass saccharifying agent of the present invention. The present invention further provides a method of manufacturing sugar from biomass, comprising using the xylanase of the present invention or the biomass saccharifying agent of the present invention.

The biomass saccharifying agent of the present invention comprises the xylanase of the present invention as an active ingredient. The biomass saccharifying agent is preferably an enzyme composition for the saccharification of biomass (which hereinafter may be referred to as an enzyme composition of the present invention). The enzyme composition of the present invention comprises the xylanase of the present invention and preferably further comprises a cellulase in terms of the improvement of the saccharification efficiency. Here, a cellulase refers to an enzyme which hydrolyzes the glycosidic bond of β-1,4-glucan of cellulose and is a generic term of enzymes called an endoglucanase, an exoglucanase or a cellobiohydrolase, and β-glucosidase etc. Examples of a cellulase used for the enzyme composition of the present invention include a commercially available cellulase preparation and a cellulase derived from an animal, a plant and a microorganism. In the enzyme composition of the present invention, such a cellulase can be used alone or in combination of 2 or more types. The cellulase preferably comprises one or more selected from the group consisting of a cellobiohydrolase and an endoglucanase in terms of the improvement of the saccharification efficiency.

In the enzyme composition of the present invention, specific examples of a cellulase which can be used in combination with the xylanase of the present invention include, without limitation, a cellulase derived from *Trichoderma reesei*; a cellulase derived from *Trichoderma viride*; a cellulase derived from a variety of *Bacillus* strains such as *Bacillus* sp. KSM-N145 (FERN P-19727), *Bacillus* sp. KSM-N252 (FERM P-17474), *Bacillus* sp. KSM-N115 (FERN P-19726), *Bacillus* sp. KSM-N440 (FERN P-19728), and *Bacillus* sp. KSM-N659 (FERN P-19730); a thermostable cellulase derived from *Pyrococcus horikoshii*; a cellulase derived from *Humicola insolens*. Among these, a cellulase derived from *Trichoderma reesei*, *Trichoderma viride* or *Humicola insolens* is preferred in terms of the improvement of the saccharification efficiency. A recombinant cellulase obtained by expressing a cellulase gene introduced exogenously into the microorganisms can be used. Specific examples include cellulase JN11 produced by X3AB1 strain (J. Ind. Microbiol. Biotechnol. (2012) 1741-9) obtained by introducing a β-glucosidase gene derived from *Aspergillus aculeatus* into *Trichoderma reesei*. Specific examples of the cellulase preparation comprising the cellulase include CELLCLAST® 1.5 L (from Novozymes), TP-60 (from Meiji), Cellic® CTec2 (from Novozymes), Accellerase™ DUET (from Genencor) and Ultra Flo® (L (from Novozymes) and these cellulase preparations can be used in combination with the xylanase of the present invention.

Specific examples of a β-glucosidase, a type of a cellulase, include a β-glucosidase derived from *Aspergillus niger* (for example, Novozyme 188 from Novozymes and a β-glucosidase from Megazyme) and a β-glucosidase derived from *Trichoderma reesei* or *Penicillium emersonii*. Among these, Novozyme 188 and a β-glucosidase derived from *Trichoderma reesei* are preferred, and a β-glucosidase derived from *Trichoderma reesei* is more preferred in terms of the improvement of the saccharification efficiency.

Specific examples of an endoglucanase, a type of a cellulase, include an enzyme derived from *Trichoderma reesei, Acremonium cellulolyticus, Humicola insolens, Clostridium thermocellum, Bacillus, Thermobifida* and *Cellulomonas*. Among these, an endoglucanase derived from *Trichoderma reesei, Humicola insolens, Bacillus* and *Cellulomonas* is preferred, and an endoglucanase derived from *Trichoderma reesei* is more preferred in terms of the improvement of the saccharification efficiency.

The enzyme composition of the present invention can comprise a hemicellulase other than the xylanase of the present invention. Here, a hemicellulase refers to an enzyme which hydrolyzes hemicellulose and is a generic term of enzymes called a xylanase, a xylosidase and a galactanase. Specific examples of a hemicellulase other than the xylanase of the present invention include a hemicellulase derived from *Trichoderma reesei*; a xylanase derived from *Bacillus* sp. KSM-N546 (FERM P-19729); a xylanase derived from *Aspergillus niger, Trichoderma viride, Humicola insolens* or *Bacillus alcalophilus*; a xylanase derived from *Thermomyces, Aureobasidium, Streptomyces, Clostridium, Thermotoga, Thermoascus, Caldocellum* or *Thermomonospora*; a β-xylosidase derived from *Bacillus pumilus*; a β-xylosidase derived from *Selenomonas ruminantium*. Among these, the enzyme composition of the present invention preferably comprises a xylanase derived from *Bacillus* sp., *Aspergillus niger, Trichoderma viride* or *Streptomyces*, or β-xylosidase derived from *Selenomonas ruminantium*, and more preferably comprises a xylanase derived from *Bacillus* sp. or *Trichoderma viride*, or a β-xylosidase derived from *Selenomonas ruminantium* in terms of the improvement of the saccharification efficiency.

The content of the xylanase of the present invention in the total protein of the enzyme composition of the present invention can be in the range of 0.1% by mass or more to 70% by mass or less. The content of the cellulase in the total protein of the enzyme composition of the present invention can be 10% by mass or more to 99% by mass or less. The content of a hemicellulase other than the xylanase of the present invention in the total protein of the enzyme composition of the present invention can be in the range of 0.01% by mass or more to 30% by mass or less. The protein content ratio of the xylanase of the present invention to the cellulase (the xylanase of the present invention/the cellulase) in the enzyme composition of the present invention can be in the range of 0.001 or more to 100 or less.

(5. Method of Manufacturing Sugar)

The method of saccharifying biomass and the method of manufacturing sugar from biomass according to the present invention comprise saccharifying biomass with the xylanase or the biomass saccharifying agent of the present invention. Examples of biomass used in the method are as described in the chapter (1. Definition) above. Wood, a processed product or a ground product of wood, and a stalk, a leaf or a bunch of a plant etc. are preferred, and bagasse, EFB, oil palm (trunk part) and Erianthus are more preferred, and bagasse is further preferred as the biomass in terms of ready availability, cost of raw materials and the improvement of the saccharification efficiency. The biomass can be used alone, or 2 or more types can be mixed to use. The biomass can be dried.

The method of saccharifying biomass and the method of manufacturing sugar of the present invention preferably comprise pretreating the biomass before the step of saccharifying biomass with the xylanase or the biomass saccharifying agent of the present invention in terms of the improvement of the grinding efficiency and the saccharification efficiency or the improvement of the sugar production efficiency of biomass (i.e. shortening of sugar production time).

Examples of the pretreatment include one or more selected from the group consisting of, for example, alkaline treatment, grinding treatment and hydrothermal treatment. Alkaline treatment is preferred as the pretreatment in terms of the improvement of the saccharification efficiency.

The alkaline treatment refers to reacting biomass with a basic compound below. Examples of a method of the alkaline treatment include a method of dipping biomass into an alkaline solution comprising a basic compound below (which hereinafter may be referred to as "dipping treatment") and a method of mixing biomass with a basic compound and subjecting the mixture to grinding treatment below (which hereinafter may be referred to as "alkali mixing grinding treatment").

The grinding treatment refers to a treatment in which biomass is made into small particles by mechanical grinding. Making biomass into small particles improves the saccharification efficiency more. Destruction of the crystal structure of cellulose comprised in biomass by the grinding treatment improves the saccharification efficiency further more. A known grinder can be used to perform the grinding treatment. The grinder used is not limited and can be any instrument as long as it can make biomass into small particles. The grinding treatment can be combined with the alkaline treatment with a basic compound. The grinding treatment can be performed before or after the alkaline treatment and alternatively can be performed simultaneously with the alkaline treatment, for example, the alkali mixing grinding treatment. In the alkali mixing grinding treatment, while for example biomass dipped into an alkaline solution can be subjected to the grinding treatment (wet grinding) or solid alkali and biomass can be subjected to grinding treatment together (dry grinding), of these, dry grinding is preferred.

The hydrothermal treatment refers to a treatment in which biomass is heat treated in the presence of moisture. The hydrothermal treatment can be performed with a known reactor and the reactor used is not specifically limited.

The method of saccharifying biomass and the method of manufacturing sugar of the present invention comprise saccharifying biomass, preferably the pretreated biomass, with the xylanase or the biomass saccharifying agent of the present invention (may be referred to herein as "saccharification treatment").

Conditions of the saccharification treatment are not specifically limited as long as the xylanase of the present invention and other enzymes used together are not inactivated. Suitable conditions can be determined by those skilled in the art as appropriate depending on the type of biomass, the procedure of a pretreatment step and the type of the enzyme used.

In the saccharification treatment, the xylanase or the biomass saccharifying agent of the present invention is preferably added to a suspension comprising biomass. The content of biomass in the suspension is preferably 0.5% by mass or more, more preferably 3% by mass or more and further preferably 5% by mass or more, and preferably 30% by mass or less, more preferably 25% by mass or less and further preferably 20% by mass or less in terms of the improvement of the saccharification efficiency or the sugar production efficiency (i.e. shortening of sugar production time).

The amount used of the xylanase or the biomass saccharifying agent of the present invention relative to the suspension is determined as appropriate depending on the pretreatment conditions as well as the type and the property of an enzyme used together and is preferably 0.001% by mass or more, more preferably 0.03% by mass or more and further preferably 0.05% by mass or more, and 100% by mass or less, more preferably 50% by mass or less and further preferably 20% by mass or less relative to the mass of biomass in terms of the mass of the xylanase of the present invention.

The reaction pH of the saccharification treatment is preferably pH 3.5 or more, further preferably pH 4.0 or more, and preferably pH 6.0 or less and more preferably pH 5.5 or less in terms of the improvement of the saccharification efficiency or the sugar production efficiency (i.e. shortening of sugar production time) and product cost reduction.

The reaction temperature of the saccharification treatment is preferably from 50 to 80° C. in terms of the improvement of the saccharification efficiency or the sugar production efficiency (i.e. shortening of sugar production time), product cost reduction and the optimum temperature of a cellulase used simultaneously. The reaction time of the saccharification treatment can be set as appropriate depending on the type or amount of biomass and the amount of the enzyme, and is preferably from 1 to 5 days, more preferably from 1 to 4 days and further preferably from 1 to 3 days in terms of the improvement of the saccharification efficiency or the sugar production efficiency (i.e. shortening of sugar production time) and product cost reduction.

As exemplary embodiments of the present invention, the following compositions, manufacturing methods, use, or methods will be further disclosed herein. However, the present invention is not limited to these embodiments.

[1] A protein consisting of an amino acid sequence described in the following (a), (b) or (c) and having xylanase activity:

(a) an amino acid sequence set forth in positions 23 to 404 of SEQ ID NO: 2;

(b) an amino acid sequence having at least 90% identity to the amino acid sequence set forth in positions 23 to 404 of SEQ ID NO: 2;

(c) an amino acid sequence modified from the amino acid sequence set forth in positions 23 to 404 of SEQ ID NO: 2 by deletion, insertion, substitution, or addition of one or more amino acids.

[2] The protein having xylanase activity according to [1], wherein the at least 90% identity is preferably 90% or more, more preferably 95% or more, further preferably 97% or more, further more preferably 98% or more, and still preferably 99% or more identity.

[3] The protein having xylanase activity according to [1], wherein the one or more amino acids are preferably 1 or more to 30 or less, more preferably 1 or more to 20 or less, further preferably 1 or more to 10 or less, and still preferably 1 or more to 5 or less.

[4] The protein having xylanase activity according to any one of [1] to [3], wherein the protein preferably has the following enzymatic properties:

70% or more of the maximal activity in the range of pH of from 4 to 5.5 at a reaction temperature of 60° C.;

Optimum reaction pH is of from 3.8 to 6.0;

Optimum reaction temperature is of from 65 to 80° C.; and

Maximal activity is 400 U/mg protein or more.

[5] A preprotein of the protein having xylanase activity according to any one of [1] to [4], wherein the preprotein consists of an amino acid sequence further comprising an amino acid sequence set forth in positions 1 to 22 of SEQ ID NO: 2 N-terminal to an amino acid sequence described in the (a), (b) or (c).

[6] A preprotein of the protein having xylanase activity according to any one of [1] to [4], wherein the preprotein consists of an amino acid sequence described in the following (a'), (b') or (c'):

(a') an amino acid sequence set forth in SEQ ID NO: 2;

(b') an amino acid sequence having at least 90% identity to the amino acid sequence set forth in SEQ ID NO: 2;

(c') an amino acid sequence modified from the amino acid sequence set forth in SEQ ID NO: 2 by deletion, insertion, substitution, or addition of one or more amino acids.

[7] A polynucleotide encoding the protein having xylanase activity according to any one of [1] to [4] or the preprotein according to [5] or [6].

[8] The polynucleotide according to [7], wherein the polynucleotide consists of a nucleotide sequence described in the following (i), (ii) or (iii):

(i) a nucleotide sequence set forth in positions 67 to 1,212 of SEQ ID NO: 1;

(ii) a nucleotide sequence having at least 90% identity to the nucleotide sequence set forth in positions 67 to 1,212 of SEQ ID NO: 1;

(iii) a nucleotide sequence modified from the nucleotide sequence set forth in positions 67 to 1,212 of SEQ ID NO: 1 by deletion, insertion, substitution, or addition of one or more nucleotides.

[9] The polynucleotide according to [7], wherein the polynucleotide consists of a nucleotide sequence described in the following (i'), (ii') or (iii'):

(i') a nucleotide sequence set forth in SEQ ID NO: 1;

(ii') a nucleotide sequence having at least 90% identity to the nucleotide sequence set forth in SEQ ID NO: 1;

(iii') a nucleotide sequence modified from the nucleotide sequence set forth in SEQ ID NO: 1 by deletion, insertion, substitution, or addition of one or more nucleotides.

[10] The polynucleotide according to [8] or [9], wherein the at least 90% identity is preferably 90% or more, more preferably 95% or more, further preferably 97% or more, further more preferably 98% or more, and still preferably 99% or more identity.

[11] The polynucleotide according to [8] or [9], wherein the one or more nucleotides are preferably 1 or more to 90 or less, more preferably 1 or more to 60 or less, further preferably 1 or more to 30 or less, further more preferably 1 or more to 15 or less, and still preferably 1 or more to 10 or less nucleotides.

[12] A vector comprising the polynucleotide according to any one of [7] to [11].

[13] A method of manufacturing a transformant, comprising introducing the polynucleotide according to any one of [7] to [11] or the vector according to [12] into a host.

[14] A transformant in which the polynucleotide according to any one of [7] to [11] or the vector according to [12] is introduced.

[15] The transformant according to [14], wherein the transformant is preferably a *Trichoderma* microorganism.

[16] A method of manufacturing a xylanase, comprising culturing the transformant according to [14] or [15].

[17] A biomass saccharifying agent comprising the protein having xylanase activity according to any one of [1] to [4].

[18] The biomass saccharifying agent according to [17], wherein the biomass saccharifying agent is an enzyme composition preferably comprising the protein having xylanase activity according to any one of [1] to [4] and a cellulase.

[19] The biomass saccharifying agent according to [18], wherein the content of the protein having xylanase activity in total protein of the enzyme composition is preferably 0.1% by mass or more to 70% by mass or less.

[20] The biomass saccharifying agent according to [18] or [19], wherein the content of the cellulase in total protein of the enzyme composition is preferably 10% by mass or more to 99% by mass or less.

[21] The biomass saccharifying agent according to any one of [18] to [20], wherein the protein content ratio of the protein having xylanase activity to the cellulase in the enzyme composition is preferably 0.001 or more to 100 or less.

[22] A method of manufacturing sugar from biomass, comprising using the protein having xylanase activity according to any one of [1] to [4] or the biomass saccharifying agent according to any one of [17] to [21].

[23] A method of saccharifying biomass, comprising using the protein having xylanase activity according to any one of [1] to [4] or the biomass saccharifying agent according to any one of [17] to [21].

[24] The method according to [22] or [23], preferably comprising saccharifying biomass with the protein having xylanase activity or biomass saccharifying agent.

[25] The method according to [24], preferably further comprising pretreating the biomass before the saccharification of biomass.

[26] The method according to [25], wherein the pretreatment is preferably one or more selected from the group consisting of alkaline treatment, grinding treatment and hydrothermal treatment.

[27] The method according to any one of [22] to [26], preferably further comprising using a cellulase.

[28] Use of the protein having xylanase activity according to any one of [1] to [4] for biomass saccharification.

[29] The use according to [28], wherein the protein is preferably combined with a cellulase.

EXAMPLES

Examples will be illustrated below to describe the present invention more specifically.

Example 1

Manufacturing of a Xylanase

A xylanase PspXyn derived from *Penicillium* sp. was manufactured.

(1) Isolation of Xylanase RNA and Synthesis of cDNA

The filamentous fungus *Penicillium* sp. isolated from soil was cultured under inducing conditions with xylan. After 4 days of culturing, the hypha and culture supernatant were obtained by filtration with Miracloth (Merck Millipore). The obtained hypha was frozen rapidly in liquid nitrogen and then disrupted using Multi-beads shocker (Yasui Kikai). An RNA solution was obtained using RNeasy Mini Kit (QIAGEN) from the obtained disrupted cells. cDNA was synthesized using Superscript II Reverse Transcriptase (Life Technologies) from the RNA solution.

(2) Production of a Vector for PspXyn Expression

An about 8.8 kbp fragment (A) was amplified by performing PCR using a forward primer 1 (SEQ ID NO: 5) and a reverse primer 1 (SEQ ID NO: 6) shown in Table 1, and using plasmid pUC-cbh1 in which a upstream to downstream region of cellobiohydrolase cbh1 derived from Trichoderma reesei (SEQ ID NO: 3) is introduced at the HincII restriction enzyme cleavage site of pUC118 (TAKARA BIO) as a template. An about 3.1 kbp fragment (B) was amplified by performing PCR using a forward primer 2 (SEQ ID NO: 7) and a reverse primer 2 shown in Table 1 (SEQ ID NO: 8), and using the acetamidase amdS derived from Aspergillus nidulans (SEQ ID NO: 4) as a template. The obtained DNA fragments (A) and (B) were processed according to the protocol of In-Fusion HD Cloning Kit (TAKARA BIO) and transformed into a competent cell E. coli HB101 (TAKARA BIO). A strain retaining a plasmid in which the gene of interest is introduced was selected by colony PCR from transformants obtained as an ampicillin resistant strain. The selected transformants were cultured using a LB agar medium (37° C., 1 day) and then the plasmid was collected from the obtained cells using High Pure Plasmid Isolation kit (Roche) and purified. The obtained vector was designated as pUC-cbh1-amdS.

An about 10 kbp fragment (C) was amplified by performing PCR using a forward primer 3 (SEQ ID NO: 9) and a reverse primer 3 (SEQ ID NO: 10) shown in Table 1, and using the pUC-cbh1-amdS as a template. An about 1.2 kbp fragment (D) of a gene region (SEQ ID NO: 1) of a PspXyn preprotein comprising a putative signal sequence (SEQ ID NO: 2) was then amplified by performing PCR using a forward primer 4 (SEQ ID NO: 11) and a reverse primer 4 (SEQ ID NO: 12) shown in Table 1, and using the cDNA obtained in the (1) as a template. The obtained DNA fragments (C) and (D) were incorporated into a vector according to the same technique as described above to produce an expression vector pUC-Pcbh1-PspXyn-amdS comprising a PspXyn gene.

(3) Production of Transformants

Transformation of a Trichoderma reesei PC-3-7 strain was performed by the vector constructed in the (2). Introduction was performed by a protoplast PEG method. Transformants were selected in a selective medium (2% glucose, 1.1 M sorbitol, 2% agar, 0.2% $KH_2PO_4$ (pH 5.5), 0.06% $CaCl_2.2H_2O$, 0.06% $CsCl_2$, 0.06% $MgSO_4.7H_2O$, 0.06% acetamide, 0.1% Trace element 1; all % are w/v %) with acetamide as a sole nitrogen source. The composition of Trace element 1 is as follows: 0.5 g $FeSO_4.7H_2O$, 0.2 g $CoCl_2$, 0.16 g $MnSO_4H_2O$, and 0.14 g $ZnSO_4.7H_2O$ diluted to 100 ml with distilled water. After the selected transformants were stabilized by subculturing, the strains stably retaining the gene of interest were further selected by colony PCR.

(4) Culturing of a Transformant

Spores of the strains selected in the (3) were inoculated into Avicel medium (1% Avicel (Sigma-Aldrich), 0.14% $(NH_4)_2SO_4$, 0.2% $KH_2PO_4$, 0.03% $CaCl_2.2H_2O$, 0.03% $MgSO_4.7H_2O$, 0.1% Bacto Polypepton, 0.05% Bacto Yeast extract, 0.1% Tween 80, 0.1% Trace element 2, and 50 mM tartaric acid buffer (pH 4.0); all % are w/v %) at $2 \times 10^5$/mL and shake cultured for 5 days at 28° C. The composition of Trace element 2 is as follows: 6 mg $H_3BO_3$, 26 mg $(NH_4)_6Mo_7O_{24}.4H_2O$, 100 mg $FeCl_3.6H_2O$, 40 mg $CuSO_4.5H_2O$, 8 mg $MnCl_2.4H_2O$, and 200 mg $ZnCl_2$ diluted to 100 ml with distilled water. The obtained culture was centrifuged and then filtered to obtain a culture supernatant comprising PspXyn.

(5) Purification of PspXyn 5 mL of the culture supernatant obtained in the (4) was buffer exchanged to 20 mM Tris-HCl (pH 8) using the desalting column Econo-Pac 10DG (BioRad). Then, purification by anion exchange was performed in the following conditions.

Instrument: HPLC fractionation system PLC-561 (GL Sciences)
Column: POROS HQ 20 μm Column 4.6×100 mm (Life Technologies)
Eluate A: 0 mM Tris-HCl buffer (pH 8)
Eluate B: 20 mM Tris-HCl buffer (pH 8) 1M NaCl
Flow rate: 1 mL/min
Monitor wavelength: 280 nm
Linear gradient: 5 min A:B=100:0,
15 min A:B=20:80

Because it was confirmed that most of the pure xylanases were contained in the peak eluted around 13 min, the fractions of from 13 to 15 min were collected, and the concentrated and desalted sample was used as a PspXyn crude enzyme solution.

Purification by gel filtration was further performed under the following conditions.

Instrument: HPLC fractionation system PLC-561 (GL Sciences)
Column: TSKgel G2000SW 21.5×300 mm (TOSOH)
Eluate: 20 mM acetate buffer (pH 5),
Flow rate: 4 mL/min,
Monitor wavelength: 280 nm Because it was confirmed that most of the pure xylanase were contained in the peak eluted around 20 min, the

TABLE 1

| Primer | Sequence | SEQ ID NO: |
|---|---|---|
| Forward primer 1 | CGTTTCCAGTGCGCAGACCGTCACAAGGGACGCAA | 5 |
| Reverse primer 1 | CCAATGATGTGCGCACTCGGCTACGTTGTCATCGT | 6 |
| Forward primer 2 | TGCGCACATCATTGGATAGG | 7 |
| Reverse primer 2 | TGCGCACTGGAAACGCAACC | 8 |
| Forward primer 3 | TAAAGCTCCGTGGCGAAAGC | 9 |
| Reverse primer 3 | GATGCGCAGTCCGCGGTTGA | 10 |
| Forward primer 4 | CGCGGACTGCGCATCATGGTTTGCTTGTCTACCAA | 11 |
| Reverse primer 4 | CGCCACGGAGCTTTAAAGACATTGCGAGTACCAAG | 12 | fractions of from 20 to 21 min were collected, and the concentrated and desalted sample was used as a PspXyn purified enzyme solution.

(6) Protein Concentration Measurement

PspXyn is a mature xylanase (an amino acid sequence set forth in positions 23-404 of SEQ ID NO: 2) in which the putative signal sequence (positions 1-22) is removed from the amino acid sequence of a xylanase preprotein (SEQ ID NO: 2). signalP (Bendtsen et al., J. Mol. Biol. 340: 783-795, 2004) was used to predict the signal sequence.

The protein concentration in the enzyme solution was measured by a UV method or a Bradford method. In the UV method, the protein concentration was determined by measuring OD280 nm. As PspXyn comprises 12 Trp residues and 18 Tyr residues and the calculated molar extinction coefficient is 92820 $M^{-1} \cdot cm^{-1}$ and the molecular weight is 40,519 g/mol, the OD280 nm at 1 mg/mL was 1.931. In the Bradford method, the protein amount was calculated based on the standard curve made using bovine γ globulin as a standard protein using Quick Start Protein assay (BioRad).

Example 2

Xylanase Activity of PspXyn (1) Arabinoxylan Degradation Activity

Wheat arabinoxylan degradation activity (XPU) of the PspXyn purified enzyme solution prepared in Example 1 (5) was measured. 1 XPU was defined as the amount of the enzyme required to release 1 micromole of a reducing sugar per minute when the enzyme produces a reducing sugar from wheat arabinoxylan as a substrate for 15 min at pH 5.0, 60° C. 100 μL of the PspXyn purified enzyme solution diluted to an appropriate concentration was mixed with 400 μL of a substrate solution (0.1 M acetate buffer (pH 5.0) comprising 0.35% wheat arabinoxylan (Megazyme)) and reacted. Before the reaction, the test tube containing the substrate solution was preincubated for 5 min at 60° C. and the diluted enzyme solution was added to the tube. The enzyme reaction was stopped by adding 0.5 mL of a DNS reagent (1.6% sodium hydroxide, 0.5% 3,5-dinitrosalicylic acid, and 30% potassium sodium tartrate) after 15 min, and then the mixture was heated at 100° C. for 5 min, and then rapidly cooled on ice. After that, 2 mL of pure water was added to the mixture and the absorbance at 540 nm was measured. A solution to which 100 μL of 50 mM acetate buffer was added instead of the diluted enzyme solution was used as a blank. The measured absorbance was calibrated based on the standard curve made using D (+) xylose and then XPU was calculated. The measurement range was from 0.01 to 0.1 XPU/mL.

The protein concentration of the PspXyn purified enzyme solution prepared in the (5) was measured by the UV method according to the procedure of Example 1 (6). Specific activity was determined from the measurements of the protein concentration and XPU. The result is shown in Table 2. The specific activity of wheat arabinoxylan degradation activity of the PspXyn purified enzyme solution at 60° C. was 561 XPU/mg. This value was 10% or more higher than that of xylanase XEA disclosed in Patent Literature 5.

TABLE 2

| Enzyme | Specific activity (XPU/mg) |
| --- | --- |
| PspXyn | 561 |

(2) Beech Wood Xylan Degradation Activity

Beech wood xylan degradation activity (U) of the PspXyn purified enzyme solution prepared in Example 1 (5) was measured. 1 U was defined as the amount of the enzyme required to release 1 micromole of a reducing sugar per minute when the enzyme produces a reducing sugar from beech wood xylan as a substrate for 15 min at pH 5.0, 60° C. 100 μL of the PspXyn enzyme solution diluted to an appropriate concentration was mixed with 900 μL of a substrate solution (0.1 M acetate buffer (pH 5.0) comprising 1% beech wood xylan (Sigma-Aldrich)) and reacted. Before the reaction, the test tube containing the substrate solution was preincubated for 5 min at 60° C. and the diluted enzyme solution was added to the tube to start the reaction. The enzyme reaction was stopped by adding 1 mL of a DNS reagent after 15 min, and then the mixture was heated at 100° C. for 5 min, and then rapidly cooled on ice. After that, 4 mL of pure water was added to the mixture and the absorbance at 540 nm was measured. A solution to which 100 μL of 50 mM acetate buffer was added instead of the enzyme solution was used as a blank. The measured absorbance was calibrated based on the standard curve made using D (+) xylose and then enzymatic activity (U) was calculated. The measurement range was from 0.01 to 0.1 U/mL.

Beech wood xylan degradation activity (U) of control xylanase Cellic® HTec (Novozymes A/S) was measured by the same procedure. The protein concentrations of the PspXyn purified enzyme solution prepared in the (5) and the Cellic® HTec were measured by Bradford method according to the procedure of Example 1 (6). Specific activities were determined from the protein concentration and enzymatic activity values. The specific activities of beech wood xylan degradation activity at 60° C. were 452 U/mg for PspXyn and 376 U/mg for Cellic® HTec. The specific activity of PspXyn was as much as 20% or more higher compared to the Cellic® HTec.

TABLE 3

| Enzyme | Specific activity (U/mg) |
| --- | --- |
| PspXyn | 452 |
| Cellic ® HTec | 376 |

Example 3

Enzymatic Properties

The arabinoxylan degradation activities of PspXyn at different conditions of pH and temperature were investigated. The arabinoxylan degradation activities of PspXyn were measured by the same method as Example 2 under different temperature conditions at pH 4 or different pH conditions at 60° C. and the relative activity under respective conditions relative to the activity under the condition which exhibited the maximal activity taken as 100% were calculated. The results are shown in Table 3 and Table 4. As shown in Table 3, the optimum temperature of PspXyn was about 75° C. As shown in Table 4, PspXyn had the optimum pH between pH 4.5 and pH 5 and had 90% or more activity of the optimum pH in the range of pH of from 4 to 5.5. This result showed that PspXyn can be used in a weak acid region.

TABLE 4

| Temperature (° C.) | Relative activity (%) |
|---|---|
| 60 | 56 |
| 65 | 73 |
| 70 | 87 |
| 75 | 100 |
| 80 | 63 |
| 85 | 19 |

TABLE 5

| pH | Relative activity (%) |
|---|---|
| 3.0 | 52 |
| 3.5 | 64 |
| 4.0 | 94 |
| 4.5 | 100 |
| 5.0 | 99 |
| 5.5 | 90 |
| 6.0 | 77 |
| 6.5 | 55 |
| 7.0 | 32 |

Example 4

Usability of PspXyn in Biomass Saccharification (1) Preparation of Biomass

Bagasse was used as biomass. The bagasse was treated in a 1% NaOH aqueous solution at 120° C. for 20 min and washed to obtain alkaline treated bagasse (composition: glucan 62.7%, xylan 17.9%). The obtained alkaline treated bagasse was used as a substrate for saccharification reaction.

(2) Preparation of a Cellulase

JN11 was used as a cellulase. JN11 was prepared by culturing a X3AB1 strain described in J. Ind. Microbiol. Biotechnol. (2012) 1741-9 in an Avicel medium by the same procedure as Example 1 (4).

(3) Saccharification Reaction 50 mg of the alkaline treated bagasse prepared in the (1) in terms of dry raw material and 0.1 mL of 1 M Sodium acetate buffer (pH 5) were added as a substrate to a screw vial with a lid (from Maruemu Corporation, No. 3, φ21×45 mm), and the JN11 (an enzyme protein amount of 2 mg/g-substrate) prepared in the (2) and the PspXyn crude enzyme solution (an enzyme protein amount of 0.1 mg/g-substrate) prepared in Example 1 (5) were added to the mixture and then water was added to the mixture to prepare a reaction solution so that the substrate concentration is 5 wt %. For comparison, a reaction solution to which JN11 and Cellic® HTec, XYN1 or XYN2 derived from *Trichoderma reesei* prepared in Comparative Example 1 below (all of which are at 0.1 mg/g-substrate) were added was prepared. As a control, a reaction solution to which only JN11 was added as an enzyme was prepared. The reaction solutions were reacted for saccharification for 3 days with reciprocally shaking at 50° C., 150 rpm. The amount of enzymes was based on the protein amount measured by the Bradford method. After the completion of the reaction, the supernatants were collected by centrifugation (15,000 rpm, 5 min, 4° C.), and the concentrations of glucose, cellobiose, xylose, xylobiose and xylotriose in the supernatants were measured by DX500 chromatography system (from Nippon Dionex K.K.), and the glucan saccharification rate, the xylan saccharification rate and the total saccharification rate were calculated by the following formulas.

Glucan saccharification rate=(amount of glucose+cellobiose in supernatant)×0.9/(amount of cellulose in a substrate)

Xylan saccharification rate=(amount of xylose+xylobiose+xylotriose in supernatant)×0.88/(amount of xylan in a substrate)

Total saccharification rate=[(amount of glucose+cellobiose in supernatant)×0.9+(amount of xylose+xylobiose+xylotriose in supernatant)×0.88]/(amount of cellulose+xylan in a substrate)

The result is shown in Table 6. The rate of saccharification of biomass was remarkably improved when the enzyme composition comprising PspXyn and a cellulase was used, compared to the case where the conventional xylanase Cellic® HTec or the xylanase derived from *Trichoderma reesei* and a cellulase were added. This result showed that PspXyn has high xylanase activity and is very suitable as an enzyme for saccharification of biomass.

TABLE 6

| Enzyme | | Glucan saccharification rate | Xylan saccharification rate | Total saccharification rate |
|---|---|---|---|---|
| JN11 2 mg/g-substrate | | 51.3% | 53.4% | 51.5% |
| JN11 2 mg/g-substrate | PspXyn 0.1 mg/g-substrate | 85.5% | 93.6% | 86.8% |
| | Cellic ® HTec 0.1 mg/g-substrate | 71.5% | 77.9% | 72.5% |
| | XYN1 0.1 mg/g-substrate | 50.3% | 54.3% | 50.9% |
| | XYN2 0.1 mg/g-substrate | 52.0% | 55.3% | 52.7% |

Comparative Example 1

Manufacturing of Xylanase XYN1 and XYN2 Derived from *Trichoderma reesei*

(1) Production of Expression Vector

An about 10 kbp fragment (E) was amplified by performing PCR using a forward primer 5 (SEQ ID NO: 15) shown in Table 7 and a reverse primer 3 (SEQ ID NO: 10) shown in Table 1, and using pUC-chh1-amdS constructed in Example 1 (2) as a template. An about 0.8 kbp fragment (F) was amplified by performing PCR using a forward primer 6 (SEQ ID NO: 16) and a reverse primer 6 (SEQ ID NO: 17) shown in Table 7, and using plasmid pUC-xyn1 in which xylanase xyn1 derived from *Trichoderma reesei* (SEQ ID NO: 13) has been introduced by the same procedure as Example 1 (2) as a template. The expression vector pUC-Pcbhi-xyn1H-amdS comprising a xyn1 gene was then produced by the method already described using the obtained DNA fragments (E) and (F). An about 0.8 kbp fragment (G) was amplified using a forward primer 7 (SEQ ID NO: 18) and a reverse primer 7 (SEQ ID NO: 19) shown in Table 7, and using plasmid pUC-xyn2 in which a xylanase xyn2 derived from *Trichoderma reesei* (SEQ ID NO: 14) has been introduced by the same procedure as a template. The expression vector pUC-Pcbh1-xyn2H-amdS comprising a xyn2 gene was then produced using the obtained DNA fragments (E) and (G).

(2) Purification of Xylanase

The *Trichoderma reesei* PC-3-7 strain was transformed with the vectors constructed in the (1) by the same procedure as Example 1 (3). The obtained transformants were cultured to produce XYN1 and XYN2, respectively, by the same procedure as Example 1 (4). XYN1 and XYN2 were purified according to the abbreviated protocol of complete His-Tag Purification Resin (Roche) from the culture supernatant comprising XYN1 or XYN2. The xylanase activity measurement confirmed that purified XYN1 and XYN2 have xylanase activity.

TABLE 7

| Primer | Sequence | SEQ ID NO: |
|---|---|---|
| Forward primer 5 | CACCACCACCACCACCACTAAAGCTCCGTGGCGAAAGC | 15 |
| Reverse primer 6 | CGCGGACTGCGCATCATGGTTGCCTTTTCCAGCCT | 16 |
| Forward primer 6 | GTGGTGGTGGTGGTGGTTGCTGACACTCTGTGAGG | 17 |
| Reverse primer 7 | CGCGGACTGCGCATCATGGTCTCCTTCACCTCCCT | 18 |
| Forward primer 7 | GTGGTGGTGGTGGTGGCTGACGGTGATGGAAGCAG | 19 |

The invention claimed is:

1. A nucleic acid construct comprising a polynucleotide encoding a protein having xylanase activity, the polynucleotide being operably linked to one or more heterologous sequences that regulate expression of the protein in an expression host or in a cell-free translation system, wherein the amino acid sequence of the protein having xylanase activity consists of an amino acid sequence selected from the group consisting of:
   (a) the amino acid sequence set forth in positions 23 to 404 of SEQ ID NO: 2;
   (b) an amino acid sequence having at least 90% sequence identity to the amino acid sequence set forth in positions 23 to 404 of SEQ ID NO: 2; and
   (c) an amino acid sequence modified from the amino acid sequence set forth in positions 23 to 404 of SEQ ID NO: 2 by deletion, insertion, substitution, or addition of no more than 30 amino acids.

2. A nucleic acid construct comprising a polynucleotide encoding a preprotein of a mature protein that has xylanase activity, the polynucleotide being operably linked to one or more heterologous sequences that regulate expression of the protein in an expression host or in a cell-free translation system, wherein the amino acid sequence of the preprotein consists of an amino acid sequence selected from the group consisting of:
(a') the amino acid sequence set forth in SEQ ID NO: 2;
(b') an amino acid sequence having at least 90% sequence identity to the amino acid sequence set forth in SEQ ID NO: 2; and
(c') an amino acid sequence modified from the amino acid sequence set forth in SEQ ID NO: 2 by deletion, insertion, substitution, or addition of no more than 30 amino acids;

wherein the amino acid sequence of the mature protein that has xylanase activity consists of an amino acid sequence selected from the group consisting of:
(a) the amino acid sequence set forth in positions 23 to 404 of SEQ ID NO: 2;
(b) an amino acid sequence having at least 90% sequence identity to the amino acid sequence set forth in positions 23 to 404 of SEQ ID NO: 2; and
(c) an amino acid sequence modified from the amino acid sequence set forth in positions 23 to 404 of SEQ ID NO: 2 by deletion, insertion, substitution, or addition of no more than 30 amino acids.

3. The nucleic acid construct of claim 1, wherein the amino acid sequence of the protein having xylanase activity is (a), the amino acid sequence set forth in positions 23 to 404 of SEQ ID NO: 2.

4. The nucleic acid construct of claim 1, wherein:
(i) amino acid sequence (a) is encoded by the nucleotide sequence set forth in positions 67 to 1,212 of SEQ ID NO: 1;
(ii) amino acid sequence (b) is encoded by a nucleotide sequence having at least 90% sequence identity to the nucleotide sequence set forth in positions 67 to 1,212 of SEQ ID NO: 1; and
(iii) amino acid sequence (c) is encoded by a nucleotide sequence modified from the nucleotide sequence set forth in positions 67 to 1,212 of SEQ ID NO: 1 by deletion, insertion, substitution, or addition of no more than 90 nucleotides.

5. The nucleic acid construct of claim 2, wherein
(i') amino acid sequence (a') is encoded by the nucleotide sequence set forth in SEQ ID NO: 1;
(ii') amino acid sequence (b') is encoded by a nucleotide sequence having at least 90% sequence identity to the nucleotide sequence set forth in SEQ ID NO: 1; and
(iii') amino acid sequence (c') is encoded by a nucleotide sequence modified from the nucleotide sequence set forth in SEQ ID NO: 1 by deletion, insertion, substitution, or addition of no more than 90 nucleotides.

6. A vector comprising a polynucleotide that encodes a protein having xylanase activity, wherein the amino acid sequence of the protein having xylanase activity consists of an amino acid sequence selected from the group consisting of (a), (b) and (c):
(a) the amino acid sequence set forth in positions 23 to 404 of SEQ ID NO: 2;
(b) an amino acid sequence having at least 90% sequence identity to the amino acid sequence set forth in positions 23 to 404 of SEQ ID NO: 2; and
(c) an amino acid sequence modified from the amino acid sequence set forth in positions 23 to 404 of SEQ ID NO: 2 by deletion, insertion, substitution, or addition of no more than 30 amino acids.

7. A method of manufacturing a transformant, comprising transforming an isolated host cell with the vector of claim 6.

8. An isolated host cell transformed with the vector of claim 6.

9. A method of manufacturing sugar from biomass, comprising adding an isolated or purified protein having xylanase activity to a suspension comprising biomass, saccharifying the biomass and producing sugar as a result of the saccharifying, wherein the amino acid sequence of the protein having xylanase activity consists of an amino acid sequence selected from the group consisting of (a), (b) and (c):
(a) the amino acid sequence set forth in positions 23 to 404 of SEQ ID NO: 2;
(b) an amino acid sequence having at least 90% sequence identity to the amino acid sequence set forth in positions 23 to 404 of SEQ ID NO: 2; and
(c) an amino acid sequence modified from the amino acid sequence set forth in positions 23 to 404 of SEQ ID NO: 2 by deletion, insertion, substitution, or addition of no more than 30 amino acids.

10. A vector comprising the nucleic acid construct of claim 2.

11. A method of manufacturing a transformant, comprising transforming an isolated host cell with the nucleic acid construct of claim 2.

12. A method of manufacturing a transformant, comprising transforming an isolated host cell with the nucleic acid construct of claim 1.

13. A method of manufacturing a transformant, comprising transforming an isolated host cell with the vector of claim 10.

14. The method of claim 9, further comprising adding to the suspension comprising biomass at least one protein selected from the group consisting of a cellulase and a hemicellulase, wherein the at least one protein is a protein other than the protein having xylanase activity.

15. An isolated host cell transformed with the nucleic acid construct of claim 2.

16. A method of producing a protein having xylanase activity, comprising culturing the host cell of claim 8 in a medium under conditions that result in producing the protein having xylanase activity.

17. A method of producing a protein having xylanase activity, comprising culturing the host cell of claim 15 in a medium under conditions that result in producing the protein having xylanase activity.

18. A vector comprising the nucleic acid construct of claim 1.

19. An isolated host cell transformed with the vector of claim 18.

20. A method of producing a protein having xylanase activity, comprising culturing the host cell of claim 19 in a medium under conditions that result in producing the protein having xylanase activity.

* * * * *

UNITED STATES PATENT AND TRADEMARK OFFICE
CERTIFICATE OF CORRECTION

PATENT NO. : 10,550,376 B2
APPLICATION NO. : 15/738211
DATED : February 4, 2020
INVENTOR(S) : Shibata et al.

Page 1 of 1

It is certified that error appears in the above-identified patent and that said Letters Patent is hereby corrected as shown below:

In the Specification

In Column 4, Line 32, delete "906" and replace it with -- 90% --.

In Column 4, Line 64, delete "pH 45" and replace it with -- pH 4~ --.

In Column 20, Line 36, (in the last line of the third column in Table 6), delete "55.3%" and replace it with -- 56.3% --.

Signed and Sealed this
Fourth Day of August, 2020

Andrei Iancu
*Director of the United States Patent and Trademark Office*